US010413495B2

(12) United States Patent
King et al.

(10) Patent No.: US 10,413,495 B2
(45) Date of Patent: Sep. 17, 2019

(54) PARTICLE BOUND PHOTOSENSITIZER MOLECULE WITH REDUCED TOXICITY

(71) Applicant: INTERNATIONAL BUSINESS MACHINES CORPORATION, Armonk, NY (US)

(72) Inventors: Scott B. King, Rochester, MN (US); Brandon M. Kobilka, Tucson, AZ (US); Joseph Kuczynski, North Port, FL (US); Jacob T. Porter, Highland, NY (US); Jason T. Wertz, Pleasant Valley, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 15/353,974

(22) Filed: Nov. 17, 2016

(65) Prior Publication Data

US 2018/0133134 A1 May 17, 2018

(51) Int. Cl.
| | |
|---|---|
| *A61K 8/40* | (2006.01) |
| *A61Q 17/04* | (2006.01) |
| *A61K 8/29* | (2006.01) |
| *A61K 8/26* | (2006.01) |
| *A61K 8/27* | (2006.01) |
| *A61K 8/19* | (2006.01) |
| *A61K 8/37* | (2006.01) |
| *A61K 8/35* | (2006.01) |
| *A61K 8/02* | (2006.01) |

(52) U.S. Cl.
CPC .............. *A61K 8/40* (2013.01); *A61K 8/0241* (2013.01); *A61K 8/19* (2013.01); *A61K 8/26* (2013.01); *A61K 8/27* (2013.01); *A61K 8/29* (2013.01); *A61K 8/35* (2013.01); *A61K 8/37* (2013.01); *A61Q 17/04* (2013.01); *A61K 2800/412* (2013.01); *A61K 2800/413* (2013.01)

(58) Field of Classification Search
CPC ........ A61K 2800/412; A61K 2800/413; A61K 8/0241; A61K 8/19; A61K 8/26; A61K 8/27; A61K 8/29; A61K 8/35; A61K 8/37; A61K 8/40; A61Q 17/04
See application file for complete search history.

(56) References Cited

U.S. PATENT DOCUMENTS

| | | | | |
|---|---|---|---|---|
| 9,907,736 | B1 * | 3/2018 | King | A61K 8/35 |
| 2001/0021375 | A1 | 9/2001 | Hossel et al. | |
| 2011/0017670 | A1 * | 1/2011 | Anderson, Jr. | B01J 20/103 210/656 |
| 2013/0078205 | A1 | 3/2013 | Dayan et al. | |
| 2015/0209260 | A1 | 7/2015 | Sayer et al. | |

FOREIGN PATENT DOCUMENTS

| | | | | |
|---|---|---|---|---|
| CN | 102675568 | A | | 9/2012 |
| CN | 104784058 | A | | 7/2015 |
| JP | 5-194932 | A | | 8/1993 |
| JP | 05194932 | A | * | 8/1993 |
| JP | 7-330567 | A | | 12/1995 |
| KR | 10-2002-0056869 | A | | 7/2002 |
| KR | 10-0481374 | B1 | | 3/2005 |
| KR | 10-2016-0031982 | A | | 3/2016 |

OTHER PUBLICATIONS

Iravani, E. et al., "Surface Modification and Spectroscopic Characterization of TiO2 Nanoparticles with 2-Aminoethyl Dihydrogen Phosphate" J. Braz. Chem. Soc. (Aug. 2015) pp. 1608-1616, vol. 26, No. 8.
"Ultrafast Photochemistry of Sunscreens" WARWICK, pp. 1-4, (Oct. 7, 2016) http://www2.warwick.ac.uk/fac/sci/moac/people/students/2013/lewis_baker/phd/ultrafast_photochemistry_sunscreens.

* cited by examiner

*Primary Examiner* — Mark V Stevens

(74) *Attorney, Agent, or Firm* — Tutunjian & Bitetto, P.C.; Nathan Rau

(57) ABSTRACT

A method for forming a photosensitizer product that is resistant to absorption by living tissue that may include binding a photosensitizer compound with an oxide-containing particle to provide the photosensitizer derivative having a microscale size, and mixing the photosensitizer derivative into a lotion. The microscale size of the photosensitizer derivative obstructs absorption by cell tissue.

9 Claims, 7 Drawing Sheets

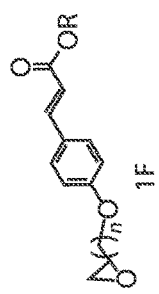
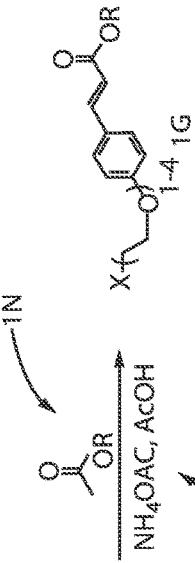
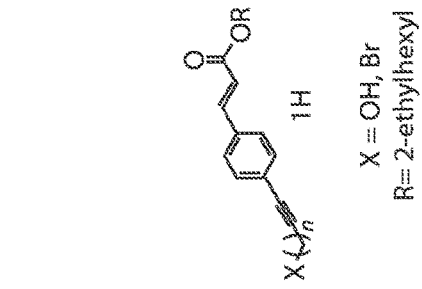
FIG. 7A
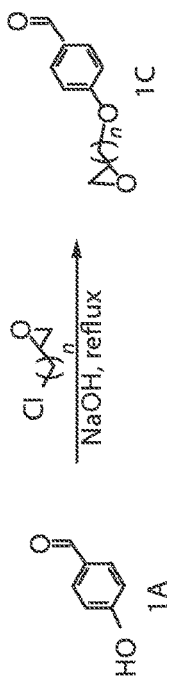
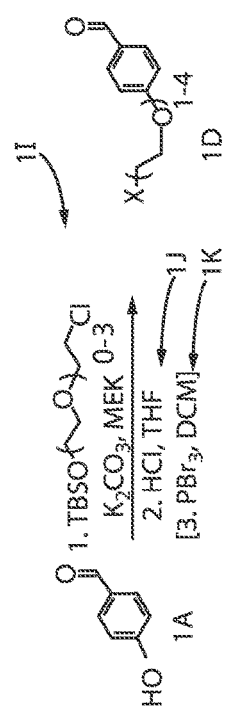
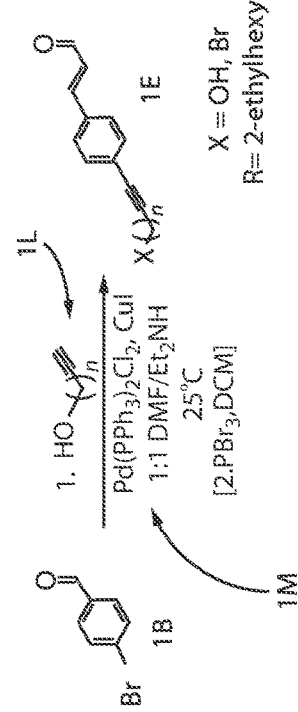
FIG. 7B
FIG. 7C

PARTICLE BOUND PHOTOSENSITIZER MOLECULE WITH REDUCED TOXICITY

BACKGROUND

Technical Field

The present disclosure generally relates to photosensitizer molecules, and more particularly to binding photosensitizer molecules to a particle to prevent leaching into the environment and to reduce the toxicity of the photosensitizer molecules.

Description of the Related Art

Sunscreens are products combining several ingredients that help prevent the sun's ultraviolet (UV) radiation from reaching the skin. Two types of ultraviolet radiation, i.e., UVA and UVB, damage the skin, age it prematurely, and increase the risk of skin cancer. It is believed that UVB is the principle form of radiation behind sunburn, while UVA rays, which penetrate the skin more deeply, are associated with wrinkling, leathering, sagging, and other light-induced effects of aging. The most common sunscreens on the market contain chemical filters that include a combination of two to six of the following active ingredients: oxybenzone, avobenzone, octisalate, octocrylene, homosalate and octinoxate. All of the sunscreens that function as chemical filters are absorbed by the skin, are hormone disruptors and/or are allergens. Consequently, a need exists to mitigate the harmful effects of active ingredients of sunscreens while maintaining the beneficial UV filtering properties of the sunscreen compositions.

SUMMARY

In accordance with an one aspect of the present disclosure, a method for forming a photosensitizer product is provided that is resistant to absorption by living tissue. In one embodiment, the method may include binding a photosensitizer compound with an oxide-containing particle to provide a photosensitizer derivative having a microscale size, and mixing the photosensitizer derivative into a lotion, wherein said microscale size obstructs absorption by cell tissue.

In another embodiment, a method for forming a photosensitizer product that is resistant to absorption by living tissue is provided that includes binding a photosensitizer derivative compound selected from the group consisting of octocrylene, octinoxate, homosalate, octisalate, and combinations thereof with an oxide-containing particle. The photosensitizer derivative with the oxide-containing particle bound thereto has a microscale size. The method may continue with mixing the photosensitizer derivative into a lotion. In some embodiments, the microscale size photosensitizer derivative having the oxide-containing particle bound thereto obstructs absorption by cell tissue.

In another embodiment, a lotion is provided that includes an active ingredient of a photosensitizer derivative compound selected from the group consisting of octocrylene, octinoxate, homosalate, octisalate, and combinations thereof. The photosensitizer derivative compound is bound to an oxide-containing particle. The compound size of the photosensitizer derivative compound that is bound to the oxide-containing particle is on a microscale. The lotion may include a lotion liquid base-containing the active ingredient mixed therein.

These and other features and advantages will become apparent from the following detailed description of illustrative embodiments thereof, which is to be read in connection with the accompanying drawings.

BRIEF DESCRIPTION OF THE DRAWINGS

The following description will provide details of preferred embodiments with reference to the following figures wherein:

FIG. 1 is a chemical structure diagram illustrating one embodiment of excited state enol to keto tautomerization that is consistent with absorbing UVA/B sunlight, in accordance with an embodiment of the present disclosure.

FIG. 2 is a chemical structure diagram illustrating one embodiment of a photochemical reaction for octocrylene.

FIG. 3 is a diagram illustrating the chemical structure of octisalate.

FIG. 4 is a diagram illustrating the chemical structure of octinoxate.

FIG. 5 is a diagram illustrating the chemical structure of octocrylene.

FIG. 6 illustrates the chemical structure of homosalate.

FIG. 7A is a chemical reaction diagram that illustrates one embodiment of a scheme for the synthesis of "tetherable" octinoxate molecule for binding to an oxide-containing particle that includes a reaction with epichlorohydrin to form a precursor that is reacted with alkyl 2-cyanate to provide the "tetherable" octinoxate, in which binding the oxide-containing particle increases the size of the particle to obstruct absorption into living tissue.

FIG. 7B is a chemical reaction diagram that illustrates one embodiment of a scheme for the synthesis of "tetherable" octinoxate for binding to an oxide-containing particle that includes a reaction with protected ethylene ether to form a precursor that is reacted with alkyl 2-cyanate to provide the "tetherable" octinoxate molecule, in which binding the oxide-containing particle increases the size of the particle to obstruct absorption into living tissue.

FIG. 7C is a chemical reaction diagram that illustrates one embodiment of a scheme for the synthesis of "tetherable" octinoxate molecule that includes a bromine functionalized precursor molecule, in which binding the oxide-containing particle increases the size of the particle to obstruct absorption into living tissue.

FIG. 8A is a chemical reaction diagram that illustrates one embodiment a scheme for the synthesis of "tetherable" octocrylene molecule for binding to an oxide-containing particle that includes a reaction with epichlorohydrin to form a precursor that is reacted with alkyl acetate to provide the "tetherable" octocrylene, in which binding the oxide-containing particle increases the size of the particle to obstruct absorption into living tissue.

FIG. 8B is a chemical reaction diagram that illustrates one embodiment of a scheme for the synthesis of "tetherable" octocrylene for binding to an oxide-containing particle that includes a reaction with protected ethylene ether to form a precursor that is reacted with alkyl acetate to provide the "tetherable" octocrylene molecule, in which binding the oxide-containing particle increases the size of the particle to obstruct absorption into living tissue.

FIG. 8C is a chemical reaction diagram that illustrates one embodiment of a scheme for the synthesis of "tetherable" octocrylene molecule that includes a bromine functionalized precursor molecule, in which binding the oxide-containing particle increases the size of the particle to obstruct absorption into living tissue.

FIG. 9A is a chemical reaction diagram that illustrates one embodiment a scheme for the synthesis of "tetherable" octisalate/homosalate molecule for binding to an oxide-containing particle that includes a reaction with epichlorohydrin, in which binding the oxide-containing particle increases the size of the particle to obstruct absorption into living tissue.

DETAILED DESCRIPTION

Detailed embodiments of the claimed structures and methods are disclosed herein; however, it is to be understood that the disclosed embodiments are merely illustrative of the claimed structures and methods that may be embodied in various forms. In addition, each of the examples given in connection with the various embodiments are intended to be illustrative, and not restrictive. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the methods and structures of the present disclosure.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Figure 1:
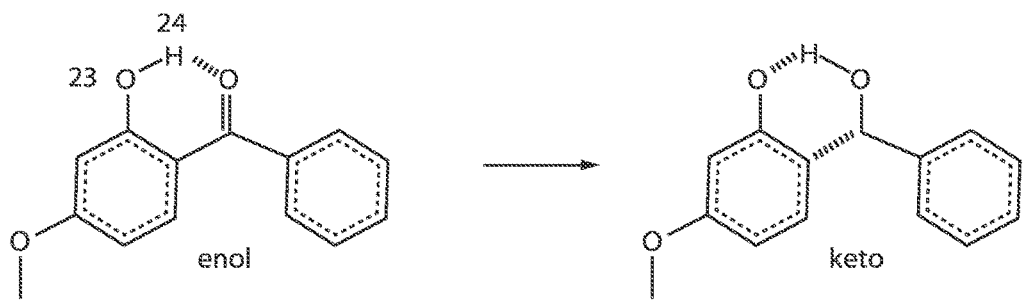
Figure 2:
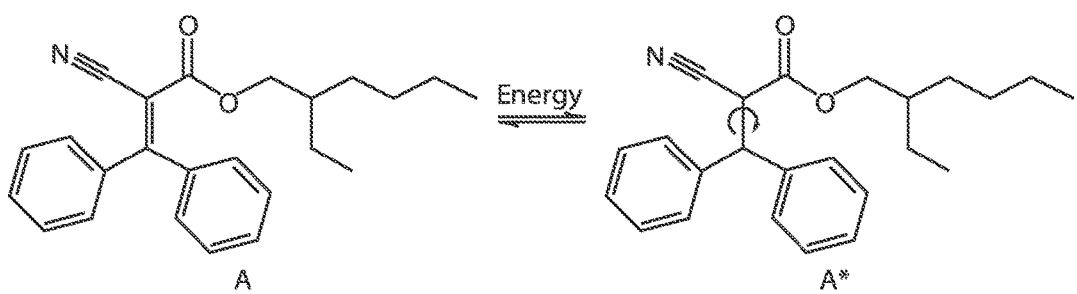
Figure 3:
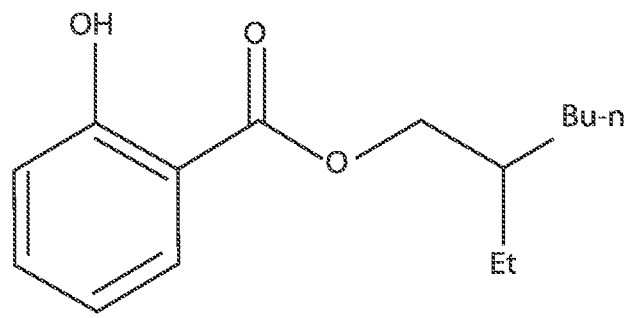
Figure 4:
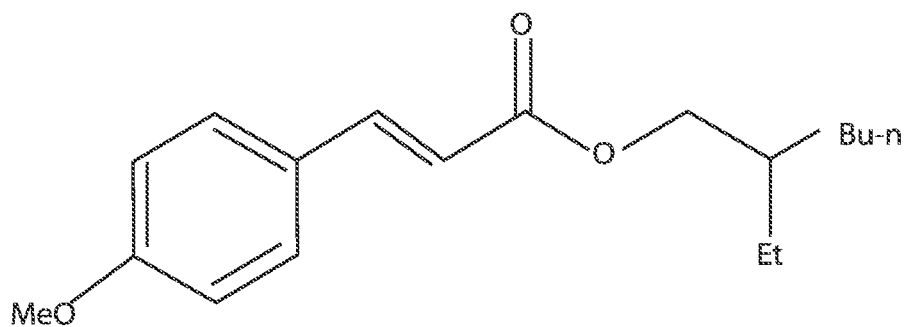

Most common sunscreens on the market contain chemical filters, which can include a combination of two to six of the following active ingredients: oxybenzone, avobenzone, octisalate, octocrylene, homosalate and octinoxate. Chemical filters function by absorbing UVA/B sunlight and converting it to vibrational energy. In some embodiments, the photoprotective properties can be understood in terms of an initial ultrafast excited state enol (identified by reference number 5) to keto (identified by reference number 10) tautomerization, as depicted in FIG. 1. This is followed by efficient internal conversion, and subsequent vibrational relaxation to the ground state (enol) tautomer. The same principles apply to octisalate, octocrylene, octinoxate, and homosalate photosensitizer molecules that are described herein. For example, the photochemical reaction of octocrylene is depicted in FIG. 2.

The present disclosure generally relates to binding active ingredients used for absorbing ultraviolet radiation, e.g., UVA and UVB radiation, to a particle to prevent leaching of the active ingredients into the environment and to prevent absorption of the active ingredients into living cells, e.g., human tissue. In some embodiments, the active ingredients that are bound to particles to reduce their toxicity in accordance with the methods described herein may include octocrylene, octinoxate, homosalate, octisalate, and/or analogous compounds. In some embodiments, the particles that may be used to bind to the aforementioned active ingredients to reduce the toxicity may be metal oxides, such a zinc oxide (ZnO) and/or titanium dioxide ($TiO_2$). In other embodiments, the particles that may be used to bind to the aforementioned active ingredients, e.g., octocrylene, octinoxate, homosalate, octisalate, and/or analogous compounds, may be ceramic microsphere, e.g., glass spheres, which are benign. By increasing the size of the compound by binding it with the oxide-containing particle, the compound can be obstructed from dermal absorption by living tissue, e.g., cells.

Octisalate ($C_{15}H_{22}O_3$), which is also referred to as octyl salicylate or 2-ethylhexyl salicylate or 2-ethylhexyl 2-hydroxybenzoate, is an ester formed by condensation of salicyclic acid with 2-ethylhexanol. FIG. 3 illustrates the chemical structure of octisalate ($C_{15}H_{22}O_3$). In FIG. 3, Et is an ethyl ($C_2H_5$) group and Bu-n is an n-butyl ($—C_4H_9$) group. The salicylate portion of the molecule absorbs ultraviolet light radiation. The range of UV spectra that is covered by octisalate is UVB. More specifically, octisalate can absorb wavelengths ranging from 295 nm to 315 nm. In other embodiments, octisalate can absorb wavelengths ranging from 307 nm to 315 nm. The ethylhexanol portion of the molecule is a fatty alcohol, which adds emollient and oil-like properties to the molecule. In some embodiments, although octisalate absorbs UVB, it does not absorb UVA. Therefore, in some embodiments, octisalate may be employed in sunscreens with other active ingredients for absorbing light, such as oxybenzone, octinoxate, homosalate, octocrylene, and/or analogous compounds, wherein the octisalate is used to augment UVB protection in the sunscreen.

One or more human case studies have shown possible photoallergic or allergenic effects associated with the typical use of octisalate. The methods and structures described herein for binding octisalate to metal inorganic particles reduce absorption of the treated octisalate into living tissue, hence substantially reducing or eliminating the aforementioned allergenic effects.

Octinoxate ($C_{18}H_{26}O_3$), which is also referred to as octyl methoxycinnamate or ethylhexyl methoxycinnamate (INCI) or (RS)-2-Ethylhexyl (2E)-3-(4-methoxyphenyl)prop-2-enoate, is an organic compound that can be used as an active ingredient in sunscreens and lip balms. FIG. 4 illustrates the chemical structure of octinoxate ($C_{18}H_{26}O_3$). In FIG. 4, Et is an ethyl ($C_2H_5$) group, Bu-n is an n-butyl ($—C_4H_9$) group, and Me is a methyl group ($CH_3$). Octinoxate is an ester formed from methoxycinnamic acid and (RS)-2-ethylhexanol. Similar to the octocrylene, octinoxate can be used in sunscreens to absorb the UVB wavelengths of the UV spectra. For example, octinoxate can absorb wavelengths ranging from 280 nm to 320 nm. In some embodiments, octinoxate does not protect against UVA. Octinoxate is a widely used UVB blocking agent in the skin care industry. As noted above, octinoxate is used in sunscreens and other cosmetics to absorb UVB rays from the sun, protecting the skin from damage, but octinoxate can also be used to reduce the appearance of scars.

In some scenarios, it is believed that octinoxate can create excess reactive oxygen species that can interfere with cellular signaling, cause mutations, lead to cell death and octinoxate has been implicated in cardiovascular disease. Further, one or more human case studies have shown possible photoallergic or allergenic effects associated with the typical use of octinoxate. The methods and structures described herein for binding octinoxate to metal inorganic particles reduce absorption of the treated octinoxate into living tissue, hence substantially reducing or eliminating the aforementioned side effects typically associated with octinoxate.

Figure 5:
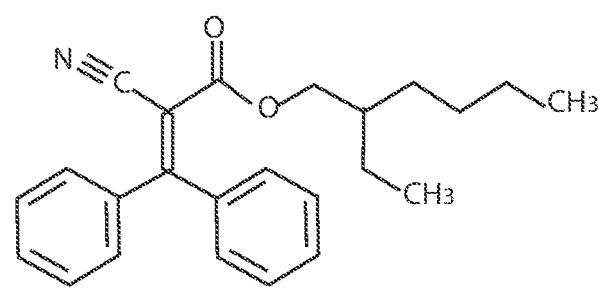

Octocrylene ($C_{24}H_{27}NO_2$), which is also referred to as 2-ethylhexyl 2-cyano-3,3-diphenyl-2-propenoate, is an ester formed by the condensation of a diphenylcyanoacrylate with 2-ethylhexanol. FIG. 5 illustrates the chemical structure of octocrylene ($C_{24}H_{27}NO_2$). The extended conjugation of the acrylate portion of the octocrylene molecule absorbs UVB and short-wave UVA (ultraviolet) rays with wavelengths from 280 to 320 nm. The ethylhexanol portion of the octocrylene molecule is a fatty alcohol, adding emollient and oil-like (water resistant) properties.

It has been determined that conventional octocrylene molecules can penetrate into the skin where they acts as a photosensitizer, which results in an increased production of free radicals under illumination. Free radicals are known to induce indirect DNA damage, and an increased concentration of free radicals might have contributed to the increased incidence of malignant melanoma in sunscreen-users compared to non-users. Further, one or more human case studies have shown possible photoallergic or allergenic effects associated with the typical use of octocrylene. The methods and structures described herein for binding octocrylene to metal inorganic particles reduce absorption of the treated octocrylene into living tissue, hence substantially reducing or eliminating the aforementioned side effects typically associated with octocrylene.

Figure 6:
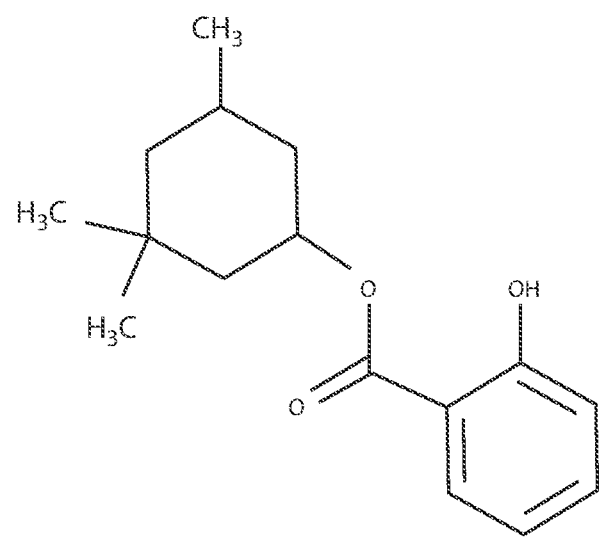

Homosalate ($C_{16}H_{22}O_3$), which is also referred to as 3,3,5-Trimethylcyclohexyl 2-hydroxybenzoate, is an ester formed from salicylic acid and 3,3,5-trimethylcyclohexanol, a derivative of cyclohexanol. FIG. 6 illustrates the chemical structure of homosalate ($C_{16}H_{22}O_3$). In some embodiments, homosalate is used as a chemical UV filter. The salicylic acid portion of the molecule absorbs ultraviolet rays with a wavelength from 295 nm to 315 nm, protecting the skin from sun damage.

In some instances, there are possible photoallergic or allergenic effects associated with the typical use of homosalate. The methods and structures described herein for binding homosalate to metal inorganic particles reduce absorption of the treated homosalate into living tissue, hence substantially reducing or eliminating the aforementioned side effects typically associated with homosalate.

It is also noted that although the following descriptions provides titanium dioxide ($TiO_2$) and zinc oxide (ZnO) as examples of oxide-containing particles that are bound to the benzophenone compound, e.g., oxybenzone compound, the present disclosure is not limited to only these metal oxides. In some examples, the oxide-containing particle is a metal oxide selected from the group consisting of titanium dioxide ($TiO_2$), tantalum oxide ($Ta_2O_5$), aluminum oxide ($Al_2O_3$), zinc oxide (ZnO), and combinations thereof. In some examples, titanium dioxide is employed, because of the non-toxic nature of the material.

In some embodiments, the titanium dioxide employed for the oxide-containing particles may be in the form of nanoparticles, i.e., particles having a nanoscale. In some examples, the oxide-containing particles having the nanoscale have a diameter that ranges from 5 nm to 100 nm. In other examples, the oxide-containing particles having a nanoscale dimension may have a diameter ranging from 10 nm to 50 nm. In further examples, the oxide-containing particles having the nanoscale dimension ranging from 15 nm to 25 nm. It is noted that the diameter of the nanoscale particles of titanium oxide may also be equal to 5 nm, 10 nm, 15 nm, 20 nm, 25 nm, 30 nm, 35 nm, 40 nm, 45 nm, 50 nm, 55 nm, 60 nm, 65 nm, 70 nm, 75 nm, 80 nm, 85 nm, 90 nm and 95 nm, as well as any range of dimensions including a lower limit and upper limit selected from the above examples.

In some embodiments, the nanoparticles of titanium dioxide that may be prepared for binding to UV absorbing active ingredients, e.g., esters, used in sunscreen and sunblock applications, such as octisalate, octocrylene, octinoxate, and homosalate, may include nano titanium dioxide having a particle size on the order of 20 nm and having a purity greater than 98%. In some examples, the purity of the titanium dioxide may be 99.5% pure.

The UV absorbing active ingredients, e.g., esters, used in sunscreen and sunblock applications, such as octisalate, octocrylene, octinoxate, and homosalate, that are described above are bound to oxide-containing particles to increase their size, in which their increased size obstructs their absorption, e.g., transdermal absorption, into living tissue. For example, in some embodiments, the methods and structures disclosed herein, and described with reference to FIGS. 6-10, derivitize octocrylene, octinoxate, homosalate, and octisalate, or an analogous compound, and bind the aforementioned derivitized UV absorbing active ingredient to an oxide-containing particle, e.g., zinc oxide (ZnO) or titanium dioxide ($TiO_2$). These derivatives, i.e., derivitized octocrylene, octinoxate, homosalate, and octisalate, possess a "tetherable" chain that can be used to bind them to the oxide-containing particles, e.g., titanium dioxide ($TiO_2$) and/or zinc oxide (ZnO). The derivitized UV absorbing active ingredients may also be referred to as derivitized photosensitizer molecules. It is also noted, that in addition to the aforementioned titanium dioxide ($TiO_2$) and zinc oxide (ZnO), the "tetherable" chains provided herein can also bind the photosensitizer to ceramic microspheres (glass spheres), such as silicon dioxide ($SiO_2$), which are benign.

FIGS. 7A-7C illustrate one embodiment of the chemical reactions for a scheme for the synthesis of "tetherable" octinoxate for binding to an oxide-containing particle, in which binding the oxide-containing particle increases the size of the particle to obstruct absorption into living tissue. Referring to FIG. 7A, a hydroxyl-functionalized precursory molecules, i.e., benzene ring functionalized molecule, identified by reference number 1A on the left side of the reaction is reacted with epichlorohydrin ($C_3H_5ClO$ or $C_3H_5OCl$) under basic conditions, e.g., in a sodium hydroxide solution (NaOH) under reflux conditions, to provide a "tetherable" precursor molecule identified by reference number 1C. In one embodiment, the hydroxyl-functionalized precursor molecule identified by reference number 1A is a benzyl aldehyde functionalized with a hydroxide (OH) group. The "tetherable" precursor molecule identified by reference number 1C can be referred to as Benzaldehyde, 4-(2-oxiranylmethoxy)-, when n=1, and can be referred to as Benzaldehyde, 4-(2-oxiranylethoxy)-, when n=2, and so forth.

Referring to FIG. 7B, in another embodiment, the hydroxyl (OH) functionalized precursor molecule identified by reference number 1A on the left side of the reaction is reacted with a protected ethylene ether to provide a "tetherable" precursor molecule identified by reference number 1D. In one embodiment, the hydroxyl-functionalized precursor molecule identified by reference number 1A is a benzyl aldehyde functionalized with a hydroxide (OH) group. The "tetherable" precursor molecule identified by reference number 1D can be referred to as Benzaldehyde, 4-(2-bromoethoxy)-, when n=1 ($C_9H_9BrO_2$), and can be referred to as Benzaldehyde, 4-(4-bromoethoxy)-, when n=2, and so forth.

More specifically, the precursor identified by reference number 1A is reacted with a [(chloroalkoxy)ethyl]trialkyl silane identified by reference number 1I which includes a tert-butyl dimethyl silyl ([—Si($CH_3)_3$]) (TBS) protecting group. In one example, the precursor identified by reference number 1A is reacted with the [(chloroalkoxy)ethyl]trialkyl silane identified by reference number 1I that includes a tert-butyl dimethyl silyl (TBS) protecting group in methyl ethyl ketone ($CH_3C(O)CH_2CH_3$)(MEK) solvent and potassium carbonate ($K_2CO_3$). In some embodiments, before the [(chloroalkoxy)ethyl]trialkyl silane identified by reference number 1I is reacted to provide the "tetherable" precursor molecule identified by reference number 1D, the silyl protecting group can then be removed under acidic conditions and functionalized to provide a bromine terminated chain. For example, the silyl protecting group may be removed using hydrochloric acid (HCl) in a solvent of tetrahydrofuran (THF) in the reaction identified by reference number 1J. THF is an organic solvent with the formula $(CH_2)_4O$. In some embodiments, the silyl protecting group is converted to a bromide. The conversion to a bromide may include reaction with phosphorus tribromide ($PBr_3$) in a solution of dichloromethane (DCM) in the reaction identified by reference number 1K. It is noted that phosphorus tribromide ($PBr_3$) is only one example of a composition for providing a bromine terminated chain. In other examples, the composition for providing the bromine terminated chain can include phosphorus pentabromide or phosphorus oxybromide.

Referring to FIG. 7C, a bromine-functionalized precursor molecule identified by reference number 1B is reacted with a terminal hydroxyl-alkyne-functionalized alkyl chain identified by reference number 1L under Sonogashira cross-coupling conditions. The Sonogashira reaction is a cross-coupling reaction to form carbon-carbon bonds that employs a palladium (Pd) catalyst to form a carbon-carbon bond between a terminal alkyne and an aryl or vinyl halide.

In some embodiments, the Sonogashira cross-coupling employs two catalysts. For example, one catalyst may be provided by a zerovalent palladium complex and a second catalyst provided by a halide salt of copper(I). Examples of such palladium catalysts include compounds in which palladium is ligated to phosphines (Pd($PPh_3)_4$). A common derivative is Pd($PPh_3)_2Cl_2$. Other examples of palladium catalysts include bidentate ligand catalysts, such as Pd(1,2-Bis(diphenylphosphino)ethane(dppe))Cl, Pd(1,3-Bis(diphenylphosphino)propane (dppp))$Cl_2$, and Pd(1,1'-Bis(diphenylphosphino)ferrocene)$Cl_2$. Examples of the second catalyst provided by a copper based material may include copper(I) salts, such as copper iodide, that react with the terminal alkyne and produce a copper(I) acetylide, which acts as an activated species for the coupling reactions. For example, Cu(I) is a co-catalyst in the reaction, and is used to increase the rate of the reaction. In one example, the Sonogashira cross-coupling reaction may include Pd($PPh_3)_2Cl_2$ and Cu(I) as identified by reference number 1M. In some embodiments, the Sonogashira cross-coupling reaction can be carried out at room temperature, e.g., 20° C. to 25° C., with a base, typically an amine, such as diethylamine ($CH_3CH_2NHCH_2CH_3$), which also acts as the solvent. The reaction medium must be basic to neutralize the hydrogen halide produced as the byproduct of this coupling reaction, so alkylamine compounds such as triethylamine and diethylamine are sometimes used as solvents, but also dimethylformamide (DMF) $(CH_3)_2NC(O)H$) or ether can be used as solvent.

Referring to FIG. 7C, reaction of the bromine functionalized precursor molecule identified by reference number 1B with the terminal hydroxyl-alkyne-functionalized alkyl chain identified by reference number 1L under the above described Sonogashira cross-coupling conditions results in the alkyl-"tetherable" photosensitizer precursor molecule identified by reference number 1E. In one embodiment, the hydroxyl-functionalized precursor molecule identified by reference number 1B is 4-bromo-benzaldehyde. The "tetherable" precursor molecule identified by reference number 1E is 4-(3-bromoprop-1yn-1-yl(benzaldehyde) when n=1, and the "tetherable" precursor molecule identified by reference number 1E is 4-(4-bromobut-1yn-1-yl(benzaldehyde) when n=2.

Referring to FIGS. 7A, 7B and 7C, the photosensitizer precursor molecules are then reacted with an alkyl 2-cyanoate to give "tetherable" octinoxate molecules. For example, the "tetherable" precursor molecule identified by reference number 1C produced from the hydroxyl functionalized precursor identified by reference number 1A reacted with epichlorohydrin under basic conditions using the reactions depicted in FIG. 7A may be reacted with a generic ester identified by reference number 1N, in which R is typically 2-ethylhexyl, to produce "tetherable" octinoxate molecules, as identified by reference number 1F. In the chemical structure identified by reference number 1F in FIG. 7A, R can be equal to, but not limited to, 2-ethylhexyl. In one embodiment, the composition of the "tetherable" octinoxate molecule identified by reference number 1F is 2-propenoic acid, 3-[4-(2-oxiranylmethoxy)phenyl] ($C_{13}H_{14}O_4$), when n=1 and R=$CH_3$, and the composition of the "tetherable" octinoxate molecule identified by reference number 1F is 2-propenoic acid, 3-[4-(2-oxiranylethoxy)phenyl] when n=2.

Referring to the reactions depicted in FIG. 7B, the "tetherable" precursor molecule identified by reference number 1D produced from the hydroxyl functionalized precursor identified by reference number 1A reacted with a protected ethylene ether may be reacted with a generic ester identified by reference number 1N, in which R is typically 2-ethylhexyl, to produce "tetherable" octinoxate molecules, as identified by reference number 1G. In one embodiment, in the "tetherable" octinoxate molecule identified by reference number 1G in FIG. 7B, R can be equal to 2-ethylhexyl, and X is equal to hydroxide (OH). In another embodiment, in the "tetherable" octinoxate molecule identified by reference number 1G in FIG. 7B, R can be equal to 2-ethylhexyl, and X is a bromide (Br). In one embodiment, the composition of the "tetherable" octinoxate molecule identified by reference number 1G is 2-propenoic acid, 3-[4-(2-bromoethoxy)phenyl]-, methyl ester, (2E), when n=1, and the composition of the "tetherable" octinoxate molecule identified by reference number 1G is 2-propenoic acid, 3-[4-(2-(2-bromoethoxy)ethoxy)phenyl]-, methyl ester, (2E), when n=2.

Referring to the reactions depicted in FIG. 7C, the "tetherable" precursor molecule identified by reference number 1E produced from the bromide functionalized precursor identified by reference number 1B reacted with the terminal hydroxyl-alkyne-functionalized alkyl chain under Sonogashira cross-coupling reactions may be reacted with a generic ester identified by reference number 1N, in which R is typically 2-ethylhexyl, to produce "tetherable" octinoxate molecules, as identified by reference number 1H. In one embodiment, in the "tetherable" octinoxate molecule identified by reference number 1H in FIG. 7C, R can be equal to 2-ethylhexyl, and X is equal to hydroxide (OH). In another embodiment, in the "tetherable" octinoxate molecule identified by reference number 1H in FIG. 7C, R can be equal to 2-ethylhexyl, and X is a bromide (Br). In one embodiment, the composition of the "tetherable" octinoxate molecule identified by reference number 1H is (E)-2-ethyhexyl 3-(4-(4-bromobut-1-yn-1-yl)phenyl)acrylate when n=2, or the composition of the "tetherable" octinoxate molecule identified by reference number 1H is (E)-2-ethyhexyl 3-(4-(4-bromoprop-1-yn-1-yl)phenyl)acrylate when n=1.

The generic ester identified by reference number 1N is reacted with the "tetherable" precursor molecule identified by reference numbers 1C, 1D, 1E in a solution of ammonium acetate ($NH_4OAC$)($NH_4CH_3CO_2$) and acetic acid ($CH_3COOH$) identified by reference number 1O, as depicted in FIGS. 7A, 7B and 7C.

Figure 10:
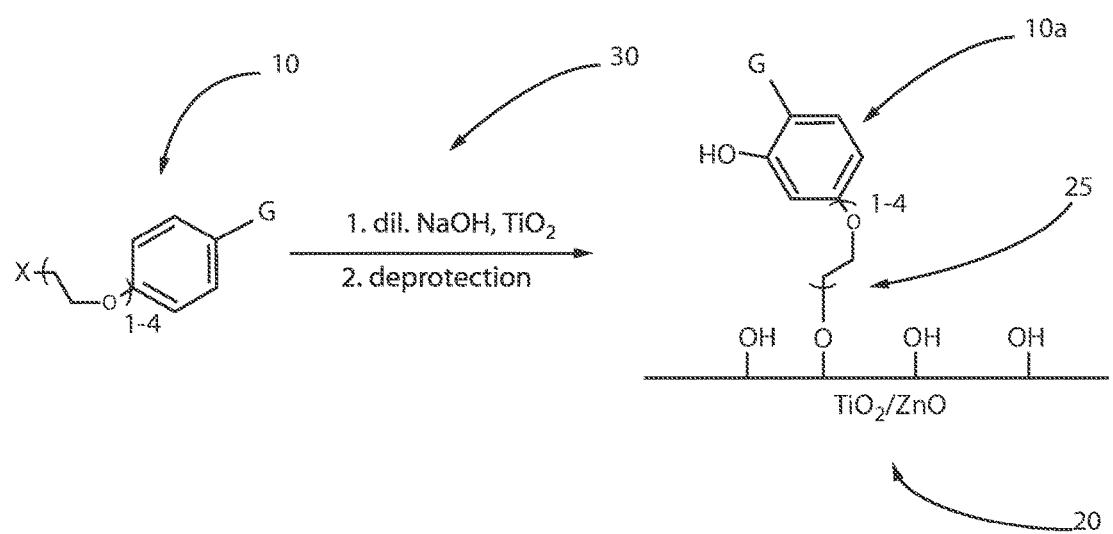
FIG. 10 illustrates one embodiment of the chemical reactions for the "tetherable" photosensitizer molecules being bound to the oxide-containing particles via nucleophilic substitution chemistry, in accordance with one embodiment of the present disclosure.

Each of the "tetherable" photosensitizer molecules in the schemes for producing the "tetherable" octinoxate molecules identified by reference numbers 1F, 1G, 1H, as depicted in FIGS. 7A, 7B and 7C, respectively, are then bound to the oxide-containing particles, e.g., titanium nanoparticle (TiNs), via nucleophilic substitution chemistry, as depicted in FIG. 10. The term "nucleophilic substitution" denotes a class of reactions in which an electron rich nucleophile selectively bonds with or attacks the positive or partially positive charge of an atom or a group of atoms to replace a leaving group.

In one embodiment, the "tetherable" octinoxate molecules identified by reference numbers 1F, 1G, 1H, as depicted in FIGS. 7A, 7B and 7C, respectively, are bound to the surface of an oxide-containing particle 20, e.g., titanium dioxide ($TiO_2$), as depicted in FIG. 10. It is noted that the "tetherable" octinoxate molecules are identified to the left of the equation depicted in FIG. 10 by reference number 10, which can be equal to any of the compositions identified by reference numbers 1F, 1G, 1H, as described above with reference to FIGS. 7A, 7B, 7C. In some embodiments, the "tetherable" octinoxate includes a terminal hydroxy group (—OH) for binding to the oxide-containing particles 20, e.g., titanium dioxide ($TiO_2$). More specifically, in some embodiments, the "tetherable" octinoxate provides for a hydroxyl-terminated chain-functionalized octocrylene bound (in which the linking molecule is identified by reference 25) to an oxide-containing particle, e.g., titanium nanoparticle.

In some embodiments, hydroxyl-terminated chain-functionalized octinoxate molecules may be dissolved or suspended in distilled water. Nano or micro titanium dioxide ($TiO_2$) may be added into the octocrylene molecules solution and may be stirred for 24 hours at room temperature, e.g., 20° C. to 25° C. The reaction mixture may contain a co-solvent such as ethanol, isopropanol, tetrahydrofuran, or ethanol to help dissolve the octinoxate molecules. Then the mixture may be centrifuged for 30 min. The resulting powders may be eluted with distilled water and, afterward, may be dried in an oven at 100° C. for 12 h. The de-protection may be provided by reaction with sodium hydroxide (NaOH) in a solvent, such as tetrahydrofuran (THF). The deprotection and binding reactions are identified by reference number 30.

The octinoxate molecules that are bound to the oxide-containing particle using the method described above with reference to FIGS. 7A-7C and FIG. 10 can provide an octinoxate-containing compound (identified by reference number 10a) having a size ranging from 10 μm to 100 μm. In other examples, the size of the octinoxate-containing compound that is bound to an oxide-containing particle, such as titanium dioxide, has a size that may be equal to 10 μm, 15 μm, 20 μm, 25 μm, 30 μm, 35 μm, 40 μm, 45 μm, 50 μm, 55 μm, 60 μm, 65 μm, 70 μm, 75 μm, 80 μm, 85 μm, 90 μm, 95 μm and 100 μm, as well as any range of dimensions having a lower value and an upper value each provided by one of the aforementioned example dimensions.

Figure 8A:
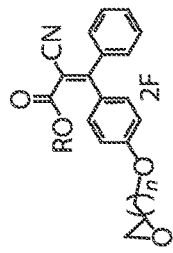
Figure 8A:
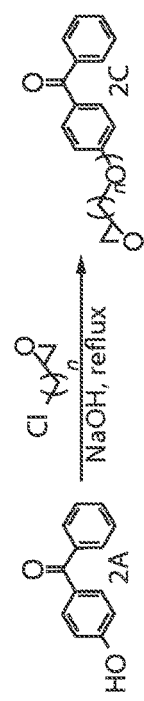
Figure 8B:
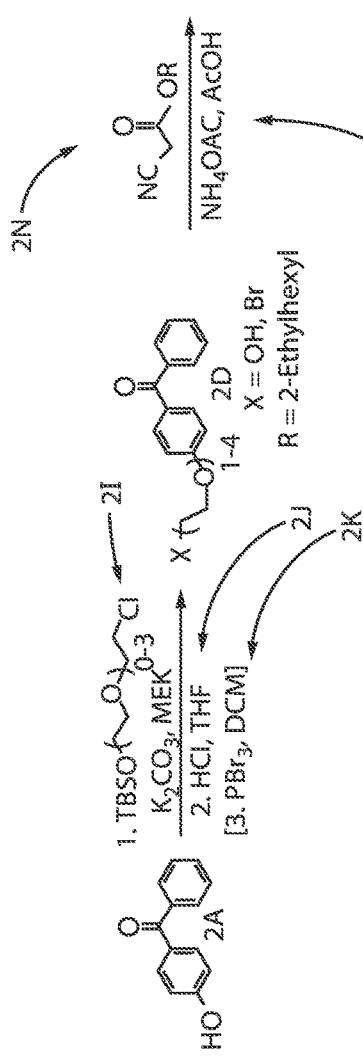
Figure 8C:
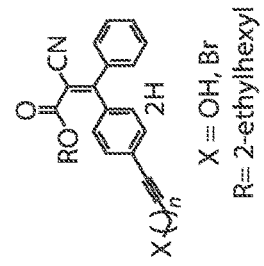
Figure 8C:
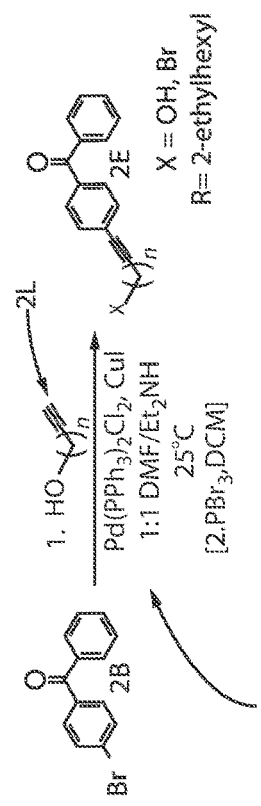

FIGS. 8A-8C illustrates one embodiment of the chemical reactions for a scheme for the synthesis of "tetherable" octocrylene for binding to an oxide-containing particle, in which binding the oxide-containing particle increases the size of the particle to obstruct absorption into living tissue. Referring to FIG. 8A, a hydroxyl-functionalized precursor molecule, i.e., a benzene ring functionalized molecule, identified by reference number 2A on the left side of the reaction, is reacted with epichlorohydrin ($C_3H_5ClO$ or $C_3H_5OCl$) under basic conditions, e.g. in a sodium hydroxide solution (NaOH) under reflux conditions, to provide a "tetherable" precursor molecule identified by reference number 2C. In one embodiment, the hydroxyl-functionalized precursory molecule identified by reference number 2A is (4-hydroxyphenyl)-phenyl methanone. In one embodiment, the "tetherable" precursor molecule identified by reference number 2C is a methanone, [4-(2-oxiranylmethoxy)phenyl]phenyl-.

Referring to FIG. 8B, in another embodiment, the hydroxyl (OH) functionalized precursor molecule identified by reference number 2A on the left side of the reaction is reacted with a protected ethylene ether to provide a "tetherable" precursor molecule identified by reference number 2D. In one embodiment, the hydroxyl-functionalized precursor molecule identified by reference number 2A is (4-hydroxyphenyl)-phenyl methanone, and the "tetherable" precursor molecule identified by reference number 2D is (4-(2-bromoethoxy)phenyl)(phenyl)methanone.

More specifically, the precursor identified by reference number 2A is reacted with [(chloroalkoxy)ethyl]trialkyl silane identified by reference number 2I that includes a tert-butyl dimethyl silyl ([—Si($CH_3$)$_3$]) (TBS) protecting group. In one example, the precursor molecule identified by reference number 2A is reacted with the [(chloroalkoxy)ethyl]trialkyl silane identified by reference number 2I that includes a tert-butyl dimethyl silyl (TBS) protecting group in a methyl ethyl ketone ($CH_3C(O)CH_2CH_3$)(MEK) solvent and potassium carbonate ($K_2CO_3$). In some embodiments, before the [(chloroalkoxy)ethyl]trialkyl silane identified by reference number 2I is reacted to provide the "tetherable" precursor molecule identified by reference number 2D, the silyl protecting group can then be removed under acidic conditions and functionalized to provide a bromine terminated chain. For example, the silyl protecting group may be removed using hydrochloric acid (HCl) in a solvent of tetrahydrofuran (THF) in the reaction identified by reference number 2J. In some embodiments, the silyl protecting group is converted to a bromide. The conversion to a bromide may include reaction with phosphorus tribromide ($PBr_3$) in a solution of dichloromethane (DCM) in the reaction identified by reference number 2K. It is noted that phosphorus tribromide (PBr$_3$) is only one example of a composition for providing a bromine terminated chain. In other examples, the composition for providing the bromine terminated chain can include phosphorus pentabromide or phosphorus oxybromide.

Referring to FIG. 8C, a bromine functionalized precursor molecule identified by reference number 2B is reacted with a terminal hydroxyl-alkyne-functionalized alkyl chain identified by reference number 2L under Sonogashira cross-coupling conditions that employs two catalysts, i.e., a palladium catalyst and a copper containing catalyst. In one example, the Sonogashira cross-coupling reaction may include Pd(PPh$_3$)$_2$Cl$_2$ and Cu(I) as identified by reference number 2M. In some embodiments, the Sonogashira cross-coupling reaction can be carried out at room temperature, e.g., 20° C. to 25° C., with a base, typically an amine, such as diethylamine (CH$_3$CH$_2$NHCH$_2$CH$_3$), which also acts as the solvent. Referring to FIG. 8C, in some embodiments, when the reaction 2M stops at "1:1 DMF/Et2NH", X═OH. In other embodiments, when the reaction 2M proceeds to "2. PBR$_3$, DCM", as depicted in FIG. 8C, X═Br.

Referring to FIG. 8C, reaction of the bromine functionalized precursor molecule identified by reference number 2B with the terminal hydroxyl-alkyne-functionalized alkyl chain identified by reference number 2L under the above described Sonogashira cross-coupling conditions results in the alkyl-"tetherable" photosensitizer precursor molecule identified by reference number 2E. In one embodiment, the hydroxyl-functionalized precursor molecule identified by reference number 2B is a benzophenone functionalized with bromide (e.g., Methanone, (4-bromophenyl)phenyl-), and the "tetherable" precursor molecule identified by reference number 2E is a (4-(3-bromoprop-1-yn-1-yl)phenyl(phenyl) methanone when n=1.

Referring to FIGS. 8A, 8B and 8C, the photosensitizer precursor molecules are then reacted with an alkyl 2-cyano ester to give "tetherable" octocrylene molecules. For example, the "tetherable" precursor molecule identified by reference number 2C produced from the hydroxyl functionalized precursor identified by reference number 2A reacted with epichlorohydrin under basic conditions using the reactions depicted the FIG. 8A may be reacted with an alkyl 2-cyano ester identified by reference number 2N, in which R is typically 2-ethylhexyl, to produce "tetherable" octocrylenes molecules, as identified by reference number 2F. In the chemical structure identified by reference number 2F in FIG. 8A, R can be equal to 2-ethylhexyl. In one embodiment, the composition of the "tetherable" octocrylene molecule identified by reference number 2F is (Z)-2-ethylhexyl 2-cyano-3-(4-(oxiran-2-ylmethoxy)phenyl)-3-phenyl)-3-phenylacrylate.

Referring to the reactions depicted in FIG. 8B, the "tetherable" precursor molecule identified by reference number 2D produced from the hydroxyl functionalized precursor identified by reference number 2A reacted with protected [(chloroalkoxy)methyl]trialkyl silane may be reacted with an alkyl 2-cyano ester identified by reference number 2N, in which R is typically 2-ethylhexyl, to produce "tetherable" octocrylene molecules, as identified by reference number 2G. In one embodiment, in the "tetherable" octocrylene molecule identified by reference number 2G in FIG. 8B, R can be equal to 2-ethylhexyl, and X is equal to hydroxide (OH). In another embodiment, in the "tetherable" octocrylene molecule identified by reference number 1G in FIG. 8B, R can be equal to 2-ethylhexyl, and X is bromine (Br). In one embodiment, the composition of the "tetherable" octocrylene molecule identified by reference number 2G is (Z)-2-ethylhexyl 3-(4-(2-bromoethoxy)phenyl)-2-cyano-3-phenylacrylate.

Referring to the reactions depicted in FIG. 8C, the "tetherable" precursor molecule identified by reference number 2E produced from the hydroxyl functionalized precursor identified by reference number 2B reacted with the terminal hydroxyl-alkyne-functionalized alkyl chain under Sonogashira cross-coupling reactions may be reacted with an alkyl acetate identified by reference number 2N, in which R is typically 2-ethylhexyl, to produce "tetherable" octocrylenes molecules, as identified by reference number 2H. In one embodiment, in the "tetherable" octocrylene molecule identified by reference number 2H in FIG. 8C, R can be equal to 2-ethylhexyl, and X is equal to hydroxide (OH). In another embodiment, in the "tetherable" octocrylene molecule identified by reference number 2H in FIG. 8C, R can be equal to 2-ethylhexyl, and X is bromine (Br). In one embodiment, the composition of the "tetherable" octocrylene molecule identified by reference number 2H is (Z)-2-ethylhexyl 3-(4-(3-bromoprop-1-yn-1-yl)phenyl)-2-cyano-3-phenylacrylate.

The alkyl acetate identified by reference number 2N is reacted with the tetherable precursor molecule identified by reference numbers 2C, 2D, 2E in a solution of ammonium acetate (NH$_4$OAC)(NH$_4$CH$_3$CO$_2$) and acetic acid (CH$_3$COOH) identified by reference number 2O, as depicted in FIGS. 8A, 8B and 8C.

Each of the "tetherable" photosensitizer molecules in the schemes for producing the "tetherable" octocrylenes molecules identified by reference numbers 2F, 2G, 2H, as depicted in FIGS. 8A, 8B and 8C, respectively, are then bound to the oxide-containing particles, e.g., titanium nanoparticle (TiNs), via nucleophilic substitution chemistry. The reactions by which the "tetherable" octocrylenes bind to oxide-containing particles is similar to the reactions by which the "tetherable" octinoxate molecules identified by reference numbers 2F, 2G, 2H are bound to the surface of an oxide-containing particle 20, as depicted in FIG. 10.

For example, in some embodiments, the "tetherable" octocrylenes include a terminal hydroxy group (—OH) for binding to the oxide-containing particles, e.g., titanium dioxide (TiO$_2$). More specifically, a hydroxyl-terminated chain-functionalized octocrylene molecule is bound to an oxide-containing particle, e.g., titanium nanoparticle.

In some embodiments, hydroxyl-terminated chain-functionalized octocrylene molecules may be dissolved or suspended in distilled water. Nano or micro titanium dioxide (TiO$_2$) may be added into the octocrylene molecules solution and may be stirred for 24 hours at room temperature, e.g., 20° C. to 25° C. The reaction mixture may contain a co-solvent such as ethanol, isopropanol, tetrahydrofuran, or ethanol to help dissolve the octocrylene molecules. Then the mixture may be centrifuged for 30 min. The resulting powders may be eluted with distilled water and, afterward, may be dried in an oven at 100° C. for 12 h. The deprotection may be provided by reaction with sodium hydroxide (NaOH) in a solvent, such as tetrahydrofuran (THF).

The octocrylene molecules that are bound to the oxide-containing particle using the method described above with reference to FIGS. 8A-8C and FIG. 10 can provide a octocrylene-containing compound having a size ranging from 10 μm to 100 μm. In other examples, the size of the octocrylene-containing compound that is bound to an oxide-containing particle, such as titanium dioxide, has a size that may be equal to 10 μm, 15 μm, 20 μm, 25 μm, 30 μm, 35 μm, 40 μm, 45 μm, 50 μm, 55 μm, 60 μm, 65 μm, 70 μm, 75 μm, 80 µm, 85 µm, 90 µm, 95 µm and 100 µm, as well as any range of dimensions having a lower value and an upper value each provided by one of the aforementioned example dimensions.

Figure 9A:
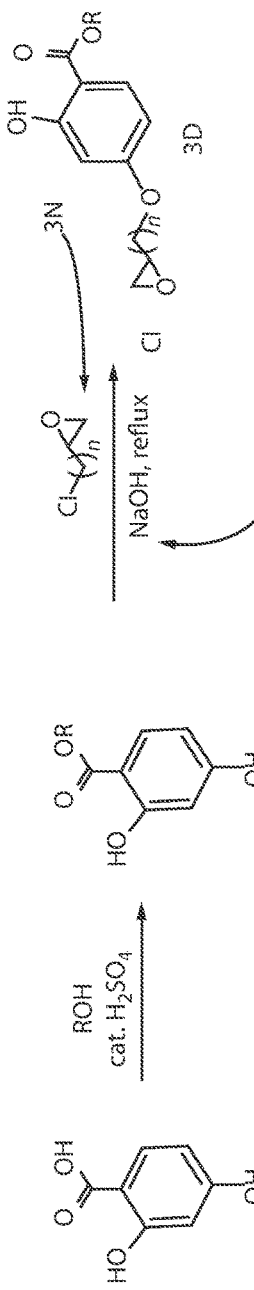
FIG. 9B is a chemical reaction diagram that illustrates one embodiment of a scheme for the synthesis of "tetherable" octisalate/homosalate molecule that is formed in a reaction with protected ethylene ether, in which binding the oxide-containing particle increases the size of the particle to obstruct absorption into living tissue.
FIG. 9C is a chemical reaction diagram that illustrates one embodiment of a scheme for the synthesis of "tetherable" octisalate/homosalate molecule that includes a bromine functionalized precursor molecule, in which binding the oxide-containing particle increases the size of the particle to obstruct absorption into living tissue.
Figure 9B:
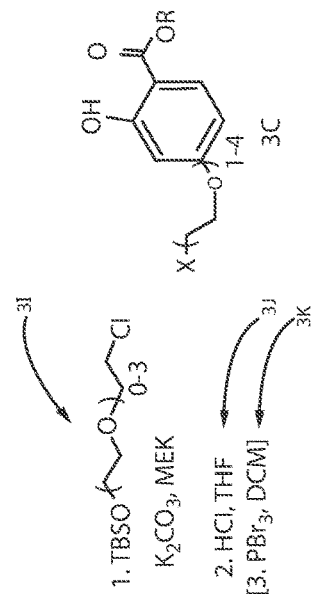
Figure 9C:
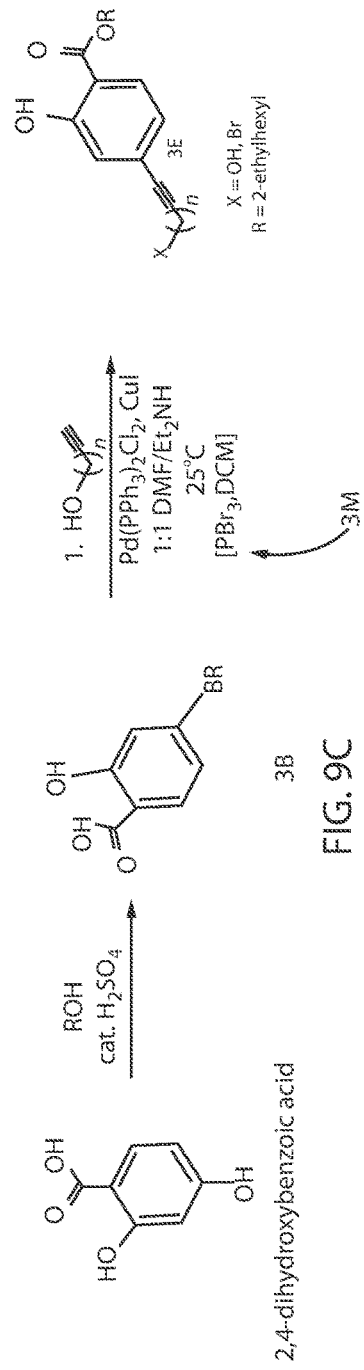

FIGS. 9A-9C illustrates one embodiment of the chemical reactions for a scheme for the synthesis of "tetherable" homosalate/octisalate for binding to an oxide-containing particle, in which binding the oxide-containing particle increases the size of the molecule to obstruct absorption into living tissue. In some embodiments, the hydroxyl-functionalized precursor molecules identified by reference number 3A in FIGS. 9A and 9B is synthesized from a commercially available benzoic acid, e.g., 2,4-dihydroxybenzoic acid. For example, the benzoic acid, e.g., 2,4-dihydroxybenzoic acid, may be reacted with ROH, in which R is equal to 2-ethylhexyl, with an acid catalyst, e.g., sulfuric acid ($H_2SO_4$), as depicted in FIGS. 9A and 9B. Referring to FIG. 9C, in some embodiments, the bromide-functionalized precursory molecules identified by reference number 3B is synthesized from a commercially available benzoic acid, e.g., 4-bromo-2-hydroxybenzoic acid. For example, the benzoic acid, e.g., 4-bromo-2-hydroxybenzoic acid, may be reacted with ROH, in which R is equal to 3,3,5-trimethylcyclohexyl, with an acid catalyst, e.g., sulfuric acid ($H_2SO_4$), as depicted in FIG. 9C.

Referring to FIGS. 9A and 9B, the hydroxide-functionalized precursor molecules identified by reference number 3A are then reacted with either epichlorohydrin under basic conditions, or a protected ethylene ether (separately functionalized to yield a bromine terminated chain) to provide the "tetherable" photosensitizer, i.e., "tetherable" homosalate/octisalate, identified by molecules 3C and 3D in FIGS. 9A and 9B.

Referring to FIG. 9A, the hydroxyl-functionalized precursory molecules, i.e., benzene ring-functionalized molecule, identified by reference number 3A on the left side of the reaction is reacted with epichlorohydrin ($C_3H_5ClO$ or $C_3H_5OCl$)(identified by reference number 3N) under basic conditions, e.g. in a sodium hydroxide solution (NaOH) under reflux conditions, to provide a "tetherable" homosalate/octisalate molecule identified by reference number 3C. In one embodiment, the "tetherable" homosalate/octisalate molecule identified by reference number 3C is a 2-ethylhexyl 2-hydroxy-4-(oxiran-2-ylmethoxy)benzoate.

Referring to FIG. 9B, in another embodiment, the hydroxyl (OH)-functionalized precursory molecule identified by reference number 3A on the left side of the reaction is reacted with a protected ethylene ether to provide a "tetherable" homosalate/octisalate molecule identified by reference number 3D. More specifically, the precursor identified by reference number 3A is reacted with ethylene ether identified by reference number 3I that includes a tert-butyl dimethyl silyl ([—Si($CH_3)_3$]) (TBS) protecting group. In one example, the precursor identified by reference number 3A is reacted with the ethylene ether identified by reference number 3I that includes a tert-butyl dimethyl silyl (TBS) protecting group in a methyl ethyl ketone ($CH_3C(O)CH_2CH_3$)(MEK) solvent and potassium carbonate ($K_2CO_3$). In some embodiments, before the ethylene ether identified by reference number 3I is reacted to provide the "tetherable" homosalate/octisalate molecule identified by reference number 3D, the silyl protecting group can be removed under acidic conditions and functionalized to provide a bromine terminated chain. For example, the silyl protecting group may be removed using hydrochloric acid (HCl) in a solvent of tetrahydrofuran (THF) in the reaction identified by reference number 3J. In some embodiments, the silyl protecting group, is converted to a bromide. The conversion to a bromide may include reaction with phosphorus tribromide ($PBr_3$) in a solution of dichloromethane (DCM) in the reaction identified by reference number 3K. It is noted that phosphorus tribromide ($PBr_3$) is only one example of a composition for providing a bromine-terminated chain. In other examples, the composition for providing the bromine terminated chain can include phosphorus pentabromide or phosphorus oxybromide. In one embodiment, the "tetherable" homosalate/octisalate molecule identified by reference number 3D is a 2-ethylhexyl 4-(2-bromoethoxy)benzoate.

Referring to FIG. 9C, the bromine-functionalized precursor molecules identified by reference number 3B are reacted with a terminal hydroxyl-alkyne-functionalized alkyl chain under Sonogashira cross-coupling conditions. This results in the alkyl-"tetherable" photosensitizer molecule 3E in FIG. 9C, which is an homosalate/octisalate "tetherable" molecule. In one embodiment, in the "tetherable" homosalate/octisalate molecule identified by reference number 3E in FIG. 9C, R can be equal to 2-ethylhexyl, and X is equal to hydroxide (OH). In another embodiment, in the "tetherable" homosalate/octisalate molecule identified by reference number 3E in FIG. 9C, R can be equal to 2-ethylhexyl, and X is a bromide (Br). In one embodiment, the composition of the "tetherable" homosalate/octisalate molecule identified by reference number 3E is 2-ethylhexyl 4-(3-bromoprop-1-yn-1-yl)benzoate.

Each of the "tetherable" homosalate/octisalate "tetherable" molecules identified by reference numbers 3C, 3D and 3E in FIGS. 9A-9C are then bound to the oxide-containing particle 20, e.g., titanium nanoparticle (TiNs), via nucleophilic substitution chemistry.

The reactions by which the "tetherable" homosalate/octisalate molecules bind to oxide-containing particles is similar to the reactions by which the "tetherable" octinoxate molecules identified by reference numbers 2F, 2G, 2H are bound to the surface of an oxide-containing particle 20, as depicted in FIG. 10.

For example, in some embodiments, the "tetherable" homosalate/octisalate molecules include a terminal hydroxy group (—OH) for binding to the oxide-containing particles, e.g., titanium dioxide ($TiO_2$). Some embodiments may also include a terminal bromine group for binding to the oxide containing particles. More specifically, in some embodiments, a hydroxyl-terminated chain-functionalized homosalate/octisalate molecule is bound to an oxide-containing particle, e.g., titanium nanoparticle. For example, hydroxyl-terminated chain-functionalized octocrylene molecules may be dissolved or suspended in distilled water. Nano or micro titanium dioxide ($TiO_2$) may be added into the octocrylene molecules solution and may be stirred for 24 hours at room temperature, e.g., 20° C. to 25° C. The reaction mixture may contain a co-solvent such as ethanol, isopropanol, tetrahydrofuran, or ethanol to help dissolve the octocrylene molecules molecule. Then the mixture may be centrifuged for 30 min. The resulted powders may be eluted with distilled water and, afterward, may be dried in an oven at 100° C. for 12 h. The de-protection may be provided by reaction with sodium hydroxide (NaOH) in a solvent, such as tetrahydrofuran (THF).

The homosalate/octisalate molecules that are bound to the oxide-containing particle using the method described above with reference to FIGS. 9A-9C and FIG. 10 can provide a homosalate/octisalate-containing compound having a size ranging from 10 µm to 100 µm. In other examples, the size of the homosalate/octisalate-containing compound that is bound to an oxide-containing particle, such as titanium dioxide, has a size that may be equal to 10 μm, 15 μm, 20 μm, 25 μm, 30 μm, 35 μm, 40 μm, 45 μm, 50 μm, 55 μm, 60 μm, 65 μm, 70 μm, 75 μm, 80 μm, 85 μm, 90 μm, 95 μm and 100 μm, as well as any range of dimensions having a lower value and an upper value each provided by one of the aforementioned example dimensions.

Any of the photosensitizer (e.g., octinoxate, octocrylene, homosalate, octisalate and combinations thereof) bound oxide-containing particles, e.g., titanium dioxide nanoparticles, can then be incorporated into sunscreen formulations either individually or in various mixtures. Other particles can be used in the place of the titanium dioxide ($TiO_2$) nanoparticles (TiNs) (i.e., glass microbeads) with a particle size large enough to prevent deep penetration into the dermal layer and absorption into the body. In another embodiment, the particle can be functionalized further at the remaining free hydroxyl groups (—OH) with other compounds as desired for sunscreen formulations by those skilled in the arts.

The sunscreen formulations suitable for use with the methods and compositions disclosed herein may include many combinations of synthetic and natural ingredients. A formulation is generally geared towards a specific SPF rating or the needs of a specific consumer group. Some embodiments employed herein include oxybenzone-containing compounds that are bound to nanoparticles of titanium dioxide for the active ingredient of the sunscreen. In addition to the sunscreening active ingredients, the formulations contemplated herein are typically emulsions such as lotions and creams, and therefore will contain several other components selected by the formulator from water, emulsifiers, emollients, fragrances, preservatives, vitamins, humectants, skin conditioners, antioxidants, waterproofing agents, and others. Antioxidants are often combined with titanium dioxide to slow down the oxidation of oils and thereby delay the deterioration of the lotion. Some examples of natural antioxidants are vitamins E and C, rice bran oil, and sesame seed oil. Another popular antioxidant in the natural category is green tea. Some sunscreen products also contain skin soothing and moisturizing additives such as aloe and chamomile.

Formulating the sunscreen lotion may begin with purifying water. Reverse osmosis extracts pure, fresh water by forcing water under pressure through a semipermeable membrane which separates pure water molecules from salts and other impurities. The active ingredients of the sunscreen lotion may then be mixed with the purified water. In some embodiments, the sunscreen lotion may be an emulsion that is formed by a process sequence that includes adding flake/powder ingredients to the oil being used to prepare the oil phase. The active ingredients may then be dispersed in the oil phase. The photosensitizer (e.g., octinoxate, octocrylene, homosalate, octisalate and combinations thereof) bound oxide-containing particles are active ingredients. A water phase containing emulsifiers and stabilizers may then be prepared. The oil (including the premixed active ingredients) and water may then be mixed to form an emulsion. Forming the emulsion can be aided by heating to between 110° F.-185° F. (45° C.-85° C.) depending on the formulation and viscosity desired. Mixing may be continued until the desired properties of the end product is provided.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Having described preferred embodiments of a composition and method (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A method for forming a photosensitizer product that is resistant to absorption by living tissue comprising:
    reacting one or more reactants from the group consisting of epichlorohydrin, protected ethylene ether, terminal hydroxyl-alkyne-functionalized alkyl chain, alkyl-2-cyanate, alkyl-2-cyanoate, alkyl acetate and combinations thereof with one or more photosensitizer compounds selected from the group consisting of octinoxate, octocrylene, octisalate, homosalate, and combinations thereof, wherein the one or more photosensitizer compounds are functionalized to react with the one or more reactants to form a tetherable structure;
    binding the tetherable structure with a metal oxide-containing particle to form a photosensitizer derivative having a microscale size ranging from 10 microns to 100 microns that obstructs absorption by cell tissue; and
    mixing the photosensitizer derivative into a lotion.

2. The method of claim 1, wherein said binding of the tetherable structure with the metal oxide-containing particle comprises a reaction of a first octinoxate precursor with the epichlorohydrin to form a second octinoxate precursor that is reacted with alkyl 2-cyanate to provide the tetherable octinoxate, wherein the tetherable octinoxate is bound to said metal oxide-containing particle.

3. The method of claim 1, wherein said binding of the tetherable structure with the metal oxide-containing particle comprises a reaction of a first octinoxate precursor with the protected ethylene ether to form a second octinoxate precursor that is reacted with alkyl 2-cyanate to provide a tetherable octinoxate, wherein the tetherable octinoxate is bound to said metal oxide-containing particle.

4. The method of claim 1, wherein said binding of the tetherable structure with the metal oxide-containing particle comprises a first octinoxate precursor that is bromide functionalized that is reacted with a terminal hydroxyl-alkyne-functionalized alkyl chain under Sonogashira cross-coupling reactions to provide a second octinoxate precursor that is reacted with the alkyl 2-cyanoate to provide a tetherable octinoxate, wherein the tetherable octinoxate is bound to said metal oxide-containing particle.

5. The method of claim 1, wherein said binding of the tetherable structure with the metal oxide-containing particle comprises a reaction of a first octocrylene precursor with the epichlorohydrin to form a second octocrylene precursor that is reacted with the alkyl acetate to provide tetherable octocrylene, wherein the tetherable octocrylene is bound to said metal oxide-containing particle.

6. The method of claim 1, wherein said binding of the tetherable structure with the metal oxide-containing particle comprises a reaction of a first octocrylene precursor with the protected ethylene ether to form a second octocrylene precursor that is reacted with the alkyl acetate to provide tetherable octocrylene, wherein the tetherable octocrylene is bound to said metal oxide-containing particle.

7. The method of claim 1, wherein said binding of the tetherable structure with the oxide-containing particle comprises a first octocrylene precursor that is bromide functionalized that is reacted with the terminal hydroxyl-alkyne-functionalized alkyl chain under Sonogashira cross-coupling reactions to provide a second octocrylene precursor that is reacted with the alkyl acetate to provide a tetherable octocrylene, wherein the tetherable" octocrylene is bound to said metal oxide-containing particle.

8. The method of claim 1, wherein said binding of the photosensitizer compound with the metal oxide-containing particle comprises a reaction of a octisalate/homosalate precursor with the protected ethylene ether to provide tetherable octisalate/homosalate, wherein the tetherable octisalate/homosalate is bound to said metal oxide-containing particle.

9. The method of claim 1, wherein said binding of the tetherable structure with the metal oxide-containing particle comprises a octisalate/homosalate precursor that is bromide functionalized that is reacted with the terminal hydroxyl-alkyne-functionalized alkyl chain under Sonogashira cross-coupling reactions to provide the tetherable octisalate/homosalate, wherein the tetherable octisalate/homosalate is bound to said metal oxide-containing particle.

* * * * *